Figure 1:
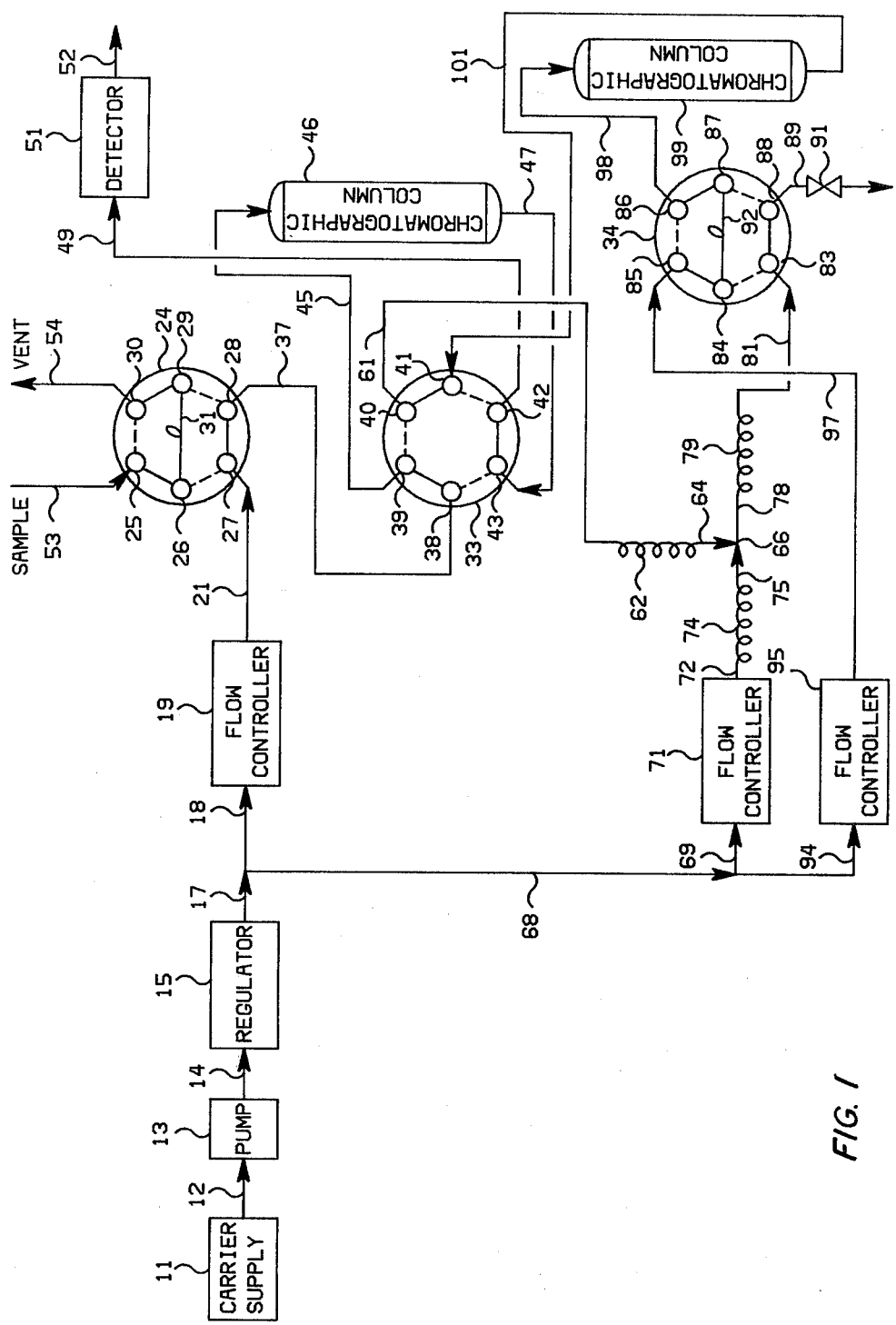

United States Patent [19]

Mowery, Jr.

[11] 4,271,697
[45] Jun. 9, 1981

[54] CHROMATOGRAPHIC ANALYSIS

[75] Inventor: Richard A. Mowery, Jr., Bartlesville, Okla.

[73] Assignee: Phillips Petroleum Company, Bartlesville, Okla.

[21] Appl. No.: 86,200

[22] Filed: Oct. 17, 1979

[51] Int. Cl.³ .............................................. G01N 31/08
[52] U.S. Cl. .............................. 73/61.1 C; 73/864.83
[58] Field of Search ............. 73/23.1, 61.1 C, 422 GC

[56] References Cited

U.S. PATENT DOCUMENTS

| 3,925,019 | 12/1975 | Small ...................................... 73/61.1 |
| 4,036,062 | 8/1976 | Cruzan . |
| 4,036,063 | 7/1977 | Roof . |
| 4,070,913 | 7/1977 | Roof . |
| 4,186,607 | 2/1980 | Porter et al. ............................ 73/61.1 |

Primary Examiner—S. Clement Swisher

[57] ABSTRACT

An analysis of the concentration of the individual components of a sample is obtained using a chromatographic analyzer where the concentrations of the individual components or the sensitivity of the detector to the individual components vary over a wide range. The sample is injected into a first chromatographic column and trace components of interest are eluted to a detector for measurement. The major components are backflushed, diluted, provided to a second chromatographic column and then eluted to a detector for measurement. The dilution of the major components ensures the linearity of the detector response. Analysis of both the trace components and major components is thus provided.

10 Claims, 1 Drawing Figure

CHROMATOGRAPHIC ANALYSIS

This invention relates to chromatography. In one aspect this invention relates to method and apparatus for analyzing a process stream where the constituents of the process stream have a wide range of concentrations and/or detector sensitivities.

A chromatographic analyzer is an analytical instrument that is used to separate in time and individually detect the constituents of a sample to be analyzed. The chromatographic analyzer typically includes an analytical column through which a carrier fluid is passed continuously. The sample to be analyzed is injected into the carrier stream and is thus carried through the analytical column. The sample constituents are carried through the analytical column at different rates and in this manner the sample constituents are separated in time into individual elution bands.

A detector is employed to detect the separated constituents and the detector output signal typically is plotted as a function of time to produce what is termed a chromatogram. As each sample component is eluted from the column, the component produces a sharp increase in the detector output signal, which in turn appears as a peak on the chromatogram.

It is often necessary to analyze a process stream to determine the concentration of various components in the process stream. If the components of interest are generally in the same range of detector sensitivity and/or concentration, then the analysis may be performed simply by eluting all of the components through a chromatographic column to a suitable detector. However, if the detector is extremely sensitive to some of the components and/or some of the components are present in significant concentrations (major components), the sample must be diluted prior to injecting the sample into the chromatographic column to ensure the linearity of the response of the detector. If the sample is not diluted, the peaks in the chromatogram may well be chopped off and thus the chromatogram will be meaningless. However, if the sample is diluted and there are components of interest present which have trace concentrations and/or for which the detector has a low sensitivity (trace components), it may well be impossible to analyze for these components once the sample is diluted.

It is thus an object of this invention to provide method and apparatus for analyzing a process stream where the constituents of the process stream have a wide range of concentrations and/or detector sensitivities.

In accordance with the present invention, method and apparatus is provided whereby a sample to be analyzed is provided to the sample loop of a first chromatographic analyzer sample valve. The first sample valve is actuated and a carrier fluid forces the sample in the sample loop through a chromatographic analyzer column valve to a first chromatographic column. The trace components of the sample are eluted from the first chromatographic column to a suitable detector.

Once the trace components of the sample have been eluted from the first chromatographic column, the column valve is actuated and the sample is backflushed from the first chromatographic column and is diluted with additional carrier. The thus-diluted sample is provided to the sample loop of a second chromatographic analyzer sample valve. The second chromatographic analyzer sample valve is actuated and carrier fluid forces the sample in the sample loop of the second chromatographic analyzer sample valve into a second chromatographic column. The remaining constituents of the sample are eluted from the second chromatographic column to the detector for measurement. In this manner, a measurement of the concentration of both trace components and major components is provided without driving the detector output past its limits.

Other objects and advantages of the invention will be apparent from the foregoing brief description of the invention and from the claims as well as from the detailed description of the drawing in which:

FIG. 1 is a diagrammatic illustration of the chromatographic analyzer sample system of the present invention.

Both the brief description of the invention and the detailed description of the invention are described in terms of eluting all of the trace components first and then backflushing the major components for further dilution. The invention is applicable to eluting part or all of the major components before the last trace component of interest is eluted. However, preferably the column packing and carrier system should be chosen so as to ensure that all of the trace components of interest are eluted before any major component is eluted. If the trace components are not eluted rapidly dilution of the trace components in the column may make subsequent analysis difficult or impossible.

The invention is described in terms of a particular apparatus configuration and particular method steps for accomplishing the desired analysis. However, the invention is applicable to any apparatus configuration and any method steps which accomplish the purpose of the present invention.

Referring now to FIG. 1, a suitable carrier fluid is contained in the carrier supply 11. The carrier fluid is provided through conduit means 12 to the pump 13. From the pump 13, the carrier fluid is provided through conduit means 14 to the pressure regulator 15. From the pressure regulator 15, the flow of the carrier fluid is to split into three separate streams. A first stream of the carrier fluid is provided through the combination of conduit means 17 and 18 to the flow controller 19. The flow controller 19 provides a smooth constant desired flow rate of the carrier fluid through conduit means 21.

Preferably only one carrier fluid is utilized. However, different carrier fluids could be utilized if desired. Care must be taken to insure that the carrier fluids are compatible and will not interfere with the analysis if more than one carrier fluid is utilized.

The sample valve 24 has six ports 25–30. The sample valve 24 is a typical sample valve such as is commonly used in chromatography. The flow of fluid through the sample valve 24 when the sample valve is in a first position is illustrated by the solid lines. When the sample valve is in a first position, port 25 is in fluid communication with port 26, port 27 is in fluid communication with port 28 and port 29 is in fluid communication with port 30. A sample loop 31 extends between port 26 and port 29. When the sample valve is in a second position, illustrated by the dotted lines, port 25 is in fluid communication with port 30, port 26 is in fluid communication with port 27 and port 28 is in fluid communication with port 29. Column valve 33 and sample valve 34 operate in substantially the same manner as sample valve 24 except that the sample loop is not present in column valve 33. Valve 33 is referred to as a "column valve" rather than a "sample valve" because of the absence of the sample loop. Hereinafter, when a sample valve or column valve is said to be in a first position the fluid flow will be through the solid lines illustrated in FIG. 1. When a sample valve or column valve is said to be in a second position the fluid flow will be through the dotted lines illustrated in FIG. 1.

Sample valve 24 and column valve 33 will be initially set to the first position. The sample valve 34 may be initially set to either the first or second positions. The carrier fluid flowing through conduit means 21 is provided to port 27 of the sample valve 24. From port 27, the carrier fluid flows to port 28 and then flows through conduit means 37 to port 38 of the sample valve 33. From port 38, the carrier fluid flows to port 39 and then flows through conduit means 45 to the inlet of the chromatographic column 46. The carrier fluid flows through the chromatographic column 46 and is provided through conduit means 47 to port 43 of the column valve 33. From port 43, the carrier fluid flows to port 42 and then flows through conduit means 49 to the detector 51. The carrier fluid is exhausted from the detector 51 through conduit means 52.

A sample to be analyzed is provided through conduit means 53 to port 25 of the sample valve 24. The sample to be analyzed flows from port 25 to port 26 and then through the sample loop 31 to the port 29. From port 29 the sample flows to port 30 and is vented through conduit means 54.

After the sample loop 31 has been filled with the sample, the sample valve 24 is actuated to the second position while the column valve 33 remains in the first position. The carrier fluid flowing through conduit means 21 is thus provided from port 27 to port 26. The carrier fluid forces the sample contained in the sample loop 31 from port 29 to port 28 and thus through conduit means 37 to port 38 of the column valve 33. The sample is thus provided to the chromatographic column 46 in the manner previously described for the carrier fluid.

The column packing of the chromatographic column 46 and the carrier fluid is preferably chosen such that the trace components of the sample will be eluted easily and will be the first to be eluted from the chromatographic column 46. These trace components are provided from the chromatographic column 46 to the detector 51 in the manner previously described. The concentrations of the trace components are measured by the detector 51 which will typically provide a chromatogram as an output.

After the trace components of the sample have been eluted from the chromatographic column 46 to the detector 51, the column valve 33 is actuated to the second position. The carrier fluid flowing through conduit means 37 thus flows from port 38 to port 43. The carrier fluid then flows through conduit means 47 and backflushes the remaining sample from the chromatographic column 46. The backflushed sample flows through conduit means 45 to port 39. From port 39 the backflushed sample flows to port 40 and is then provided through conduit means 61 to the resistor 62. The resistor 62 will typically be a coiled length of small diameter tubing. From the resistor 62, the backflushed sample flows through conduit means 64 to node 66.

Carrier fluid is provided from the regulator 15 through the combination of conduit means 17, 68 and 69 to the flow controller 71. The flow controller 71 provides a smooth, desired flow rate of carrier fluid through conduit means 72 to the resistor 74 which is also typically a coiled length of small diameter tubing. From the resistor 74, the carrier fluid flows through conduit means 75 to node 66. The carrier fluid is mixed with the backflushed sample and is provided through conduit means 78 to the resistor 79 which is also typically a coiled length of small diameter tubing. The resistor 79 provides a more thorough mixing of the backflushed sample and the carrier fluid flowing thorough conduit means 75. From the resistor 79, the thus-diluted sample flows through conduit means 81 to port 83 of the sample valve 34. With the sample valve 34 in the first position, the diluted sample flows from port 83 to port 88 and is exhausted through conduit means 89 in which control valve 91 is operably located.

The sample valve 34 is switched to the second position to fill the sample loop 92 with the diluted sample. Once the sample loop 92 has been filled with the diluted sample, the control valve 34 is actuated to the first position.

A carrier fluid is provided from the regulator 15 through a combination conduit means 17, 68 and 94 to the flow controller 95. From the flow controller 95, the carrier fluid flows through conduit means 97 to port 85 of the sample valve 34. With the sample valve 34 in the first position, the carrier fluid flows from port 85 to port 84 and forces the diluted sample from the sample loop 92 to port 87 and thus to port 86 of the sample valve 34. From port 86, the diluted sample flows through conduit means 98 to the chromatographic column 99. The remaining constituents in the diluted sample are eluted from the chromatographic column 99 and flow through conduit means 101 to port 41 of the column valve 33. With the column valve 33 in the second position, the eluted components flowing from the chromatographic column 99 flow to port 42 and are then provided through conduit means 49 to the detector 51. The detector 51 analyzes the major components in the sample and will again typically provide a chromatogram as an output.

The present invention is primarily applicable to the automatic analysis of process streams over a long term. The constituents of interest in the process stream should be known and it is merely the concentration of the constituents that is being measured. The present invention has little applicability in the art of analyzing to determine what constituents are present in a sample.

To set up the present analysis technique for a particular process stream, a carrier fluid and a packing for chromatographic column 46 are first chosen which will preferably enable the elution of the trace components quickly and easily. The sample is then provided to the chromatographic column 46 and the components of the sample are allowed to elute from the chromatographic column 46 with the response to detector 51 being monitored. The time required for a component to elute which has a concentration and/or detector sensitivity which cannot be handled by the detector 51 is monitored. Once this time has been determined, the column valve 33 is simply switched to the second position prior to that time. This ensures that a component having too large a concentration and/or detector sensitivity will not be eluted from the chromatographic column 46.

The backflushed components of the sample are then diluted by some amount. The thus-diluted sample is analyzed and again the detector response is monitored. If the dilution is sufficient to ensure the linearity of the output from the detector 51, then this dilution will be utilized. The amount of the dilution may be varied simply by increasing or decreasing the flow of carrier fluid through conduit means 72. The resistors 62 and 74 may also be sized to provide a particular ratio between the flow of the sample flowing through conduit means 64 and the carrier fluid flowing through conduit means 75. Once the desired dilution of the major components has been determined, the system is then ready for use on a particular process stream.

The detector 51 may be any suitable detector. The most commonly utilized detector is an ultraviolet detector but other detectors may be utilized if desired.

Any suitable flow controller may be utilized to provide a constant desired flow flow rate. Presently preferred is a Model LC221S flow controller manufactured by Veriflow Corp., 250 Canal Blvd., Richmond, VA.

Any suitable chromatographic analyzer sample valve may be utilized. Presently preferred is the Model 8 sample valve manufactured by Applied Automation Inc., Bartlesville, OK. A Model 8 sample valve without the sample loop is utilized as the column valve.

Any suitable flow rate of the carrier fluid from the flow controllers may be utilized. Typically, a flow rate in the rage of about 1 to about 1.5 cc/min. will be utilized.

The flow restrictions may have any desired diameter. Typically, the flow restrictions have a diameter in the range of about 0.01 inch (0.254 mm) to about 0.005 inch (0.127 mm). Typically the length of the flow restrictions 62 and 64 will be varied to provide the desired dilution of the sample flowing through the flow restriction 62. The length of the flow restriction 79 may be varied to provide a desired degree of mixing. The flow restrictions are coiled to provide a long length in a small volume.

Other components of the chromatographic analyzer system are components which are commonly used in chromatographic analysis and are readily available from a plurality of suppliers.

While the invention has been described in terms of the presently preferred embodiment, reasonable variations and modifications are possible by those skilled in the art, within the scope of the described invention and the appended claims. Variations such as using different carrier fluids, different detectors, or different sample valve configurations are within the scope of the present invention.

That which is claimed is:

1. Apparatus for determining the concentration of at least two components in a sample fluid wherein at least one of said components has a low value of concentration and/or detector sensitivity and at least one of said components has a high value of concentration and/or detector sensitivity, said apparatus comprising:
   a first chromatographic separation column means;
   means for passing a first stream of carrier fluid to said first chromatographic separation column means;
   means for injecting said sample fluid into said first stream of carrier fluid flowing to said first chromatographic separation column means;
   a detector means;
   means for passing the at least one component of said sample fluid, which has said low value, from said first chromatographic separation column means to said detector means, said detector means providing at least one first response representative of the concentration of the at least one component of said sample fluid, which has said low value, provided from said first chromatographic separation column means to said detector means;
   dilution means;
   means for passing the at least one component of said sample fluid, which has said high value, from said first chromatographic separation column means to said dilution means;
   means for passing a second stream of carrier fluid to said dilution means;
   a second chromatographic separation column means;
   means for passing a third stream of carrier fluid to said second chromatographic separation column means;
   means for injecting the diluted at least one component of said sample fluid, which has said high value, into said third stream of carrier fluid flowing to said second chromatographic separation column means; and
   means for passing the diluted at least one component of said sample fluid, which has said high value, from said second chromatographic separation column means to said detector means, said detector means providing at least one second response representative of the concentration of the diluted at least one component of said sample fluid, which has said high value.

2. Apparatus in accordance with claim 1 wherein said dilution means comprises:
   a first coiled conduit means having a diameter in the range of about 0.01 (0.254 mm) inch to about 0.005 (0.127 mm) inch;
   a second coiled conduit means having a diameter in the range of about 0.01 (0.254 mm) to about 0.005 (0.127 mm) inch, said at least one component of said sample fluid, which has said high value, flowing through said first coiled conduit means, said second stream of carrier fluid flowing through said second coiled conduit means, the said at least one component of said sample fluid, which has said high value, being combined with said second stream of carrier fluid flowing through said second coiled conduit means after the at least one component of said sample fluid which has said high value, has passed through said first coiled conduit means and said second stream of carrier fluid has passed through said second coiled conduit means;
   a third coiled conduit means having a diameter in the range of about 0.01 (0.254 mm) inch to about 0.005 (0.127 mm) inch; and
   means for passing the mixture of said second stream of carrier fluid, which flowed through said second coiled conduit means, and the at least one component of said sample fluid, which has said high value and which flowed through said first coiled conduit means, through said third coiled conduit means.

3. Apparatus in accordance with claim 2 wherein said means for injecting said sample fluid into said first stream of carrier fluid flowing to said first chromatographic separation column means is a first chromatographic analyzer sample valve and said means for injecting the diluted at least one component of said sample fluid, which has said high value, into said third stream of carrier fluid flowing to said second chromatographic separation means is a second chromatographic analyzer sample valve.

4. Apparatus in accordance with claim 3 wherein said means for passing the at least one component of said sample fluid, which has said high value, from said first chromatographic separation column means to said dilution means comprises means for backflushing the at least one component of said sample fluid, which has said high value, from said first chromatographic separation column means to said dilution means.

5. Apparatus comprising:
   a first sample valve means having first, second, third, fourth, fifth and sixth ports, said first port being in fluid communication with said second port, said third port being in fluid communication with said fourth port, and said fifth port being in fluid communication with said sixth port when said frst sample valve means is in a first position, said first port being in fluid communication with said sixth port, said second port being in fluid communication with said third port and said forth port being in fluid communication with said fifth port when said first sample valve means is in a second position, a sample loop extending between said second port and said fifth port;
   a column valve means having first, second, third, fourth, fifth and sixth ports, said first port being in fluid communication with said second port, said third port being in fluid communication with said fourth port, and said fifth port being in fluid communication with said sixth port when said second sample valve means is in a first position, said first port being in fluid communication with said sixth port, said second port being in fluid communication with said third port and said fourth port being in fluid communication with said fifth port when said second sample valve means is in a second position;
   a first conduit means for supplying a first stream of carrier fluid to the third port of said first sample valve means;
   a second conduit means for supplying a sample fluid to the first port of said first sample valve means, said sample fluid flowing from said first port to said second port and thus through said sample loop of said first sample valve means when said first sample valve means is in the first position;
   a third conduit means extending from the fourth port of said first sample valve means to the second port of said column valve means, said first stream of carrier fluid flowing through the sample loop of said first sample valve means to force the sample fluid contained in the sample loop of said first sample valve means from said first sample valve means to the second port of said column valve means when said first sample valve means is in the second position;
   a first chromatographic separation column means;
   fourth conduit means extending from the first port of said column valve means to the inlet of said chromatographic separation column means, the fluid flowing through said third conduit means being provided to the inlet of said chromatographic separation column means when said column valve means is in the first position;
   fifth conduit means extending from the outlet of said chromatographic separation column means to the third port of said column valve means;
   a detector means;
   sixth conduit means extending from the fourth port of said column valve means to the inlet of said detector means, at least one component of said sample fluid, which has a low value of concentration and/or detector sensitivity, being provided from the outlet of said first chromatographic separation column means to the inlet of said detector means when said column valve means is in the first position, said detector means providing at least one first response representative of the concentration of the at least one component in said sample fluid, which has said low value, provided from said first chromatographic separation column means, said column valve means being actuated to the second position when the at least one component of said sample fluid, which has a low value, has eluted from said first chromatographic separation column means;
   a dilution means;
   seventh conduit means extending from the sixth port of said column valve means to said dilution means, at least one component of said sample fluid, which has a high value of concentration and/or detector sensitivity, being backflushed from said chromatographic separation column means and provided to said dilution means when said column valve means is in the second position;
   eighth conduit means for supplying a second stream of carrier fluid to said dilution means;
   a second sample valve means having first, second, third, fourth, fifth and sixth ports, said first port being in fluid communication with said second port, said third port being in fluid communication with said fourth port, and said fifth port being in fluid communication with said sixth port when said second sample valve means is in a first position, said first port being in fluid communication with said sixth port, said second port being in fluid communication with said third port and said fourth port being in fluid communication with said fifth port when said second sample valve means is in a second position, a sample loop extending between said second port and said fifth port;
   ninth conduit means extending from said dilution means to the third port of said second sample valve means;
   tenth conduit means for supplying a third stream of carrier fluid to the first port of said second sample valve means;
   a second chromatographic separation column means;
   eleventh conduit means extending from the sixth port of said second sample valve means to the inlet of said second chromatographic separation column means, the diluted at least one backflushed component of said sample fluid flowing through the sample loop of said second sample valve means when said second sample valve means is in the second position, the diluted at least one backflushed component of said sample fluid being provided to the inlet of said second chromatographic separation column means when said second sample valve means is in the first position; and
   twelfth conduit means extending from the outlet of said second chromatographic separation column means to the fifth port of said column valve means, the diluted at least one backflushed component of said sample fluid being provided from the outlet of said second chromatographic separation column means to the inlet of said detector means when said column valve means is in the second position, said detector means providing at least one second response representative of the concentration of the diluted at least one backflushed component in said sample fluid.

6. Apparatus in accordance with claim 5 wherein said means for diluting the at least one backflushed component of said sample fluid comprises:
- a first coiled conduit means having a diameter in the range of about 0.01 (0.254 mm) inch to about 0.005 (0.127 mm) inch, the at least one backflushed component of said sample fluid passing from said seventh conduit means through said first coiled conduit means;
- a second coiled conduit means having a diameter in the range of about 0.01 (0.254 mm) inch to about 0.005 (0.127 mm) inch, said second stream of carrier fluid passing from said eighth conduit means through said second coiled conduit means, the at least one backflushed component of said sample fluid being combined with said second stream of carrier fluid flowing through said second coiled conduit means after the at least one backflushed component of said sample fluid has passed through said first coiled conduit means and said second stream of carrier fluid has passed through said second coiled conduit means;
- a third coiled conduit means having a diameter in the range of about 0.01 (0.254 mm) inch to about 0.005 (0.127 mm) inch; and
- means for passing the mixture of said second stream of carrier fluid which flowed through said second coiled conduit means and the at least one backflushed component of said sample fluid which flowed through said first coiled conduit means through said third coiled conduit means.

7. Apparatus in accordance with claim 6 additionally comprising:
- a first flow controller operably located in said first conduit means;
- a second flow controller operably located in said eighth conduit means; and
- a third flow controller operably located in said tenth conduit means.

8. A method for determining the concentration of at least two components in a sample fluid wherein at least one of said components has a low value of concentration and/or detector sensitivity and at least one of said components has a high value of concentration and/or detector sensitivity, said method comprising the steps of:

- passing a first stream of carrier fluid to a first chromatographic separation column means;
- injecting said sample fluid into the first stream of carrier fluid flowing to said first chromatographic separation column means;
- withdrawing a first effluent stream containing at least one component of said sample fluid, having said low value, from said first chromatographic separation column means and passing the thus withdrawn first effluent stream to a detector which provides at least one first response representative of the concentration of the at least one component of said sample fluid, having said low value, provided from said first chromatographic separation column means;
- withdrawing a second effluent stream containing at least one component of said sample fluid, having said high value, from said first chromatographic separation column means;
- diluting at least a portion of the thus withdrawn second effluent stream containing at least one component of said sample fluid having said high value;
- passing a second stream of carrier fluid to a second chromatographic separation column means;
- injecting the thus diluted portion into the second stream of carrier fluid flowing to said second chromatographic separation column means; and
- passing the second stream of carrier fluid containing the diluted at least one component of said sample fluid, having said high value, from said second chromatographic separation column means to a detector means which provides at least one second response representative of the concentration of the diluted at least one component of said sample fluid having said high value.

9. A method in accordance with claim 8 wherein said step of diluting the at least one component of said sample fluid, having said high value, comprises mixing the at least one component of said sample fluid, having said high value, with carrier fluid.

10. A method in accordance with claim 7 wherein a first plurality of components of said sample fluid, having said low value, are provided from said first chromatographic separation column means to said detector means and a second plurality of components of said sample fluid, having said high value, are withdrawn from said first chromatographic separation column means by backflushing.

* * * * *